US00PP11484P

United States Patent [19]

McGredy

[11] Patent Number: Plant 11,484

[45] Date of Patent: Aug. 15, 2000

[54] HYBRID TEA ROSE PLANT NAMED 'MACTAURANG'

[75] Inventor: Samuel D. McGredy, Auckland, New Zealand

[73] Assignee: Bear Creek Gardens, Inc., Medford, Oreg.

[21] Appl. No.: 09/205,052

[22] Filed: Dec. 3, 1998

[51] Int. Cl.[7] ..... A01H 5/00

[52] U.S. Cl. ..... Plt./130

[58] Field of Search ..... Plt./130, 132, 134, Plt./136, 137, 138

*Primary Examiner*—Howard J. Locker

*Attorney, Agent, or Firm*—Klarquist Sparkman Campbell Leigh & Whinston, LLP

[57] ABSTRACT

A hybrid tea rose plant having tall, upright growing habit; dark green, glossy foliage; coral orange and light yellow striped flower (upper surface); light yellow petal reverse; long cutting stems; and resistance to rose rust.

1 Drawing Sheet

The present invention relates to a new and distinct variety of rose plant of the hybrid tea class which was originated by me by crossing the variety 'MACerupt' (not patented), with an unnamed seedling whose parentage is MACbupal (not patented) × unnamed seedling of Stars 'n' Stripes (not patented).

The primary objective of this breeding was to produce a tall, healthy, upright growing hybrid tea rose with striped flowers. The objective was substantially achieved, along with other desirable improvements, as evidenced by the following unique combination of characteristics that are outstanding in the new variety and that distinguish it from its parents, as well as from all other varieties of which I am aware:

1. Tall, upright growing plant;
2. Dark green, glossy foliage;
3. Coral orange and light yellow striped flower (upper surface);
4. Light yellow petal reverse;
5. Long cutting stems; and
6. Resistance to rose rust.

'MACtaurang' is a very vigorous, tall growing garden hybrid tea. It is very novel in flower color being both a bicolor rose and a striped rose.

Asexual reproduction of this new variety by budding, as performed at Wasco, Calif., and at Auckland, New Zealand, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'MACerupt' (not patented).

*Pollen parent.*—Unnamed seedling (MACbupal (not patented) × unnamed seedling of Stars 'n' Stripes (not patented)).

Classification:

*Botanical.*—*Rosa hybrida.*

*Commercial.*—Hybrid Tea.

FLOWER

Observations made from specimens grown in a garden environment at Somis, Calif. from January 1996 to October 1998.

Blooming habit: Continuous.

Bud:

*Size.*—1¾ to 2 inches long when the petals start to unfurl.

*Form.*—The bud form is long, pointed ovoid to globular broad based.

*Color.*—When sepals first divide, the bud color is Yellow Group 4D with some coloration of Red Group 46C on the petals. When half blown, the upper sides of the petals are Red Group 43C with stripes of Yellow Group 4D. The innermost petals not exposed to the sun are much more yellow in color (Yellow Group 4D) and have stripes of Red Group 43C. The lower sides of the petals are Yellow Group 4C.

*Sepals.*—Color: Green Group 138B and when exposed to bright sun often have a bronze cast to them of Greyed Red Group 181B. Surface texture: Covered with many fine hairs. There are three normally appendaged sepals. There are two unappendaged sepals with hairy edges.

*Receptacle.*—Color: Green Group 137C. Shape: Apple. Size: Medium (5/16" long × ¼" wide). Surface: Smooth.

*Peduncle.*—Length: Medium (averaging 3½ to 4"). Surface: Smooth. Color: Yellow Green Group 146C and when exposed to bright sun often have a bronze cast to them of Greyed Red Group 181C. Strength: Stiff, erect.

Bloom:

*Size.*—Large. Average open size is 4½ to 5".

*Borne.*—Singly.

*Stems.*—Strength: Strong. Average length is 18–22".

*Form.*—When first open: High centered. Permanence: Retains its form to the end. Outer petals curl back.

*Petalage.*—Number of petals under normal conditions: 35

*Color.*—The upper sides of the petals are Red Group 43C with stripes of Yellow Group 4D. The innermost petals are much more yellow (Yellow Group 4D) with stripes of Red Group 43C. The reverse sides of the petals are Yellow Group 4C. The base of each petal has an intense Yellow Group 13A half moon ¼"×¼" in size. The major color on the upper side is Red Group 43C.

*Variegations.*—Only as described above.

*Discoloration.*—At the end of the first day: No change. At the end of the third day: No change. By day four the flower is half open and exposure to the sun increases the spread of Red Group 43C color to all petals and not just the outer petals.

*Fragrance.*—Moderate. Fruity.

Petals:

*Texture.*—Thick.

*Shape.*—Round to somewhat oval.

*Form.*—Tips slightly recurved. Edges slightly quilled.

*Arrangement.*—Imbricated. Petaloids in the center: None.

*Persistence.*—Petals drop off cleanly before drying.

*Lastingness.*—On the plant: Long (six to seven days). As a cut flower: Long (eight to nine days).

Reproductive parts:

*Anthers.*—Size: Medium. Quantity: Many. Color: Yellow. Arrangement: Regular around styles.

*Filaments.*—Color: Yellow.

*Pollen.*—Color: Gold.

*Styles.*—Color: Yellow.

*Stigmas.*—Color: Greenish-white.

Plant:

*Form.*—Bush.

*Growth.*—Very vigorous; upright; branching;

*Mature plant.*—Height, after one full season, is 5½–6', and width is 3½–4'.

Foliage: Number of leaflets on normal mid-stem leaves: Five.

*Size.*—Large (6 on 6½" long × 5½" wide.).

*Quantity.*—Abundant.

*Color.*—New foliage: Upper and lower surfaces: Greyed-Orange Group 176B. Old foliage: Upper Surface: Green Group 139A. Lower Surface: Green Group 139C.

*Shape.*—Broadly oval.

*Texture.*—Upper side: Leathery and glossy.

*Edge.*—Serrated.

*Serration.*—Single, Small.

*Petiole rachis.*—Color: Greyed-Red 178B (upper surface). Yellow-Green Group 147B on lower surface.

*Petiole underside.*—Smooth with occasional prickle.

*Stipules.*—Long (¾"); serrated, bearded.

*Disease resistance.*—Susceptible to mildew and blackspot. Resistant to rust.

Wood:

*New wood.*—Color: Reddish (Greyed-Orange Group 176B). Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Medium; hooked slightly downward.

*Color when young.*—Greyed-Orange Group 176A.

*Color when mature.*—Greyed-Orange Group 166B.

Small prickles:

*Quantity.*—On main stalks: None. On laterals: None.

I claim:

1. A new and distinct variety of rose plant of the hybrid tea class, substantially as herein shown and described, characterized particularly as to novelty by its tall, upright growing habit; dark green, glossy foliage; coral orange and light yellow striped flower (upper surface); light yellow petal reverse; long cutting stems; and resistance to rose rust.

* * * * *

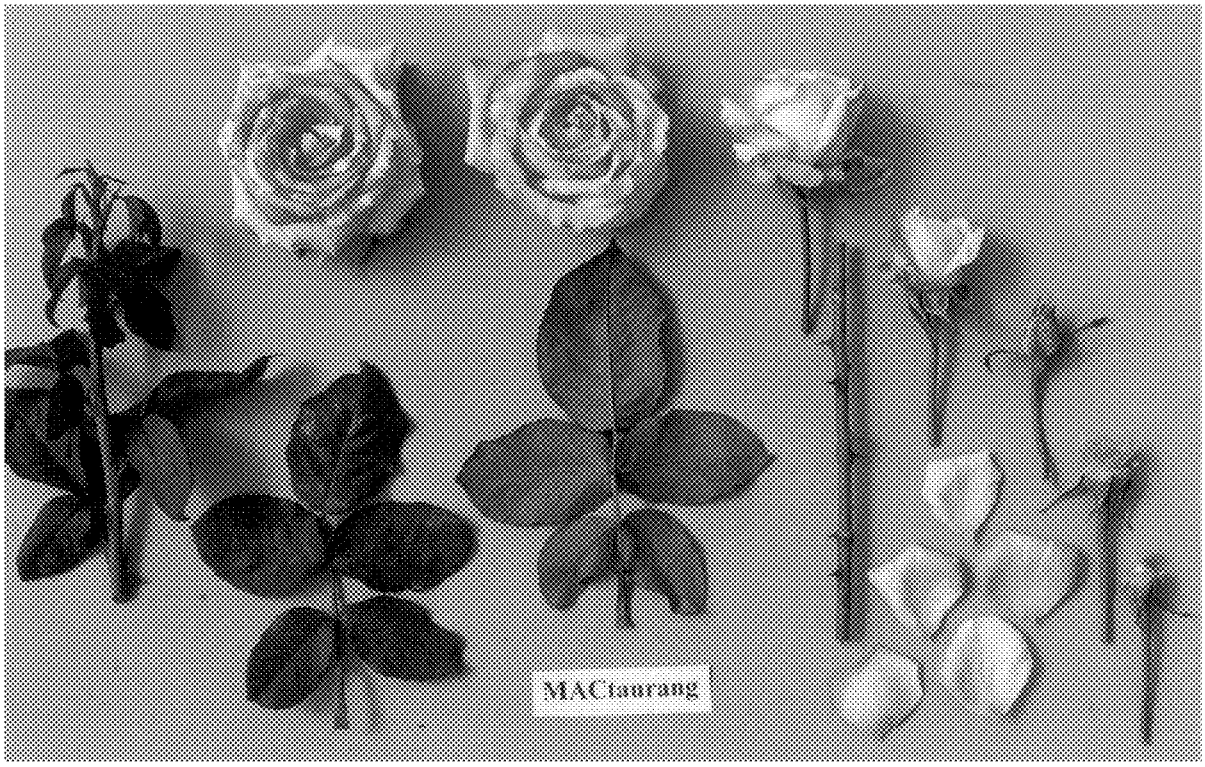
MACtaurang

UNITED STATES PATENT AND TRADEMARK OFFICE

CERTIFICATE OF CORRECTION

PATENT NO. : PP 11,484
DATED : August 15, 2000
INVENTOR(S) : Samuel D. McGredy

It is certified that error appears in the above-identified patent and that said Letters Patent is hereby corrected as shown below:

Column 3,
Line 33, change "(6 on 6½" long x 5½" wide)" to (6 to 6½" long x 5 to 5½" wide) --, as shown on Page 4, line 27 of the Application.

Signed and Sealed this

First Day of January, 2002

*Attest:*

*Attesting Officer*

JAMES E. ROGAN
*Director of the United States Patent and Trademark Office*